US 7,766,832 B2

(12) United States Patent
Okamura et al.

(10) Patent No.: US 7,766,832 B2
(45) Date of Patent: Aug. 3, 2010

(54) ULTRASONIC DIAGNOSTIC DEVICE AND IMAGE PROCESSING DEVICE

(75) Inventors: Yoko Okamura, Otawara (JP); Masatoshi Nishino, Otawara (JP); Jiro Higuchi, Otawara (JP); Tetsuya Higashi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 745 days.

(21) Appl. No.: 11/549,787

(22) Filed: Oct. 16, 2006

(65) Prior Publication Data
US 2007/0100237 A1 May 3, 2007

(30) Foreign Application Priority Data
Oct. 17, 2005 (JP) ............................. 2005-302189

(51) Int. Cl.
*A61B 8/00* (2006.01)
(52) U.S. Cl. ....................................... 600/438; 600/440
(58) Field of Classification Search ................. 600/437, 600/438, 440–443, 454–456, 301; 73/95, 73/789, 573
See application file for complete search history.

(56) References Cited

U.S. PATENT DOCUMENTS 5,495,771 A * 3/1996 Sumi et al. .................... 73/789

| 5,524,636 | A | * | 6/1996 | Sarvazyan et al. | ........... 600/587 |
| 6,099,471 | A | * | 8/2000 | Torp et al. | .................... 600/438 |
| 2002/0178833 | A1 | * | 12/2002 | Chen et al. | ..................... 73/795 |
| 2004/0059224 | A1 | | 3/2004 | Varghese et al. | |
| 2006/0058592 | A1 | * | 3/2006 | Bouma et al. | ................ 600/301 |

FOREIGN PATENT DOCUMENTS

| DE | 198 24 108 A1 | 12/1999 |
| JP | 5-184576 | 7/1993 |
| JP | 2004-261198 | 9/2004 |
| JP | 2006-20801 | 1/2006 |
| JP | 2006-26079 | 2/2006 |
| WO | WO 2006/013916 A1 | 2/2006 |

OTHER PUBLICATIONS

K. Waki, et al., "Study of Distortion Rate in Real-time Tissue Elastography", Ulrtrasonic Medicine, Extra Issue of vol. 32, Apr. 15, 2005, pp. 3.
K. Waki, et al., "Real-time Tissue Elastography", Jpn J Med Ultrasonics., vol. 32, p. 292, (2006).

* cited by examiner

*Primary Examiner*—Eric F Winakur
*Assistant Examiner*—Lawrence N Laryea
(74) *Attorney, Agent, or Firm*—Oblon, Spivak, McClelland, Maier & Neustadt, L.L.P.

(57) ABSTRACT

A means to which at least two ROIs are input, a calculating means that calculates strain values of tissue with respect to the at least two ROIs by applying a pressure onto an object, and a display means that displays the strain values of the at least two ROIs so as to be compared with each other are comprised.

9 Claims, 4 Drawing Sheets

FIG. 4

```

# Patient ID: BREAST-a
# Patient Name: - -
# Date: 20050225
# Time: 16:35:04
# TCA Data Source: Strain(Lagrangian)[-]
# Number of Curves: 6
# Derivative Pitch: 3.0mm
# Number of Points in Curve: 15
```

ROI INFORMATION →

| [msec] | 1 | 2 | 3 | 4 | 5 | 6 |
|---|---|---|---|---|---|---|
| 0.00 | -0.00 | -0.00 | -0.00 | -0.00 | -0.00 | -0.00 |
| 38.50 | -0.00 | -0.00 | -0.00 | -0.00 | -0.00 | -0.00 |
| 77.00 | -0.00 | -0.00 | -0.00 | -0.00 | -0.00 | -0.00 |
| 115.50 | -0.00 | -0.00 | -0.00 | -0.00 | -0.00 | -0.00 |
| 154.00 | -0.01 | -0.00 | -0.00 | -0.00 | -0.01 | -0.00 |
| 192.50 | -0.01 | -0.00 | -0.01 | -0.00 | -0.01 | -0.00 |
| 231.00 | -0.01 | -0.01 | -0.01 | -0.00 | -0.01 | -0.00 |
| 269.49 | -0.01 | -0.01 | -0.01 | -0.00 | -0.01 | -0.00 |
| 307.99 | -0.02 | -0.01 | -0.01 | -0.00 | -0.01 | -0.01 |
| 346.49 | -0.02 | -0.01 | -0.01 | -0.01 | -0.01 | -0.01 |
| 384.99 | -0.02 | -0.01 | -0.02 | -0.00 | -0.01 | -0.01 |
| 423.49 | -0.02 | -0.01 | -0.02 | -0.01 | -0.02 | -0.01 |
| 461.99 | -0.02 | -0.01 | -0.02 | -0.01 | -0.02 | -0.01 |
| 500.49 | -0.02 | -0.01 | -0.02 | -0.01 | -0.02 | -0.01 |
| 538.99 | -0.02 | -0.01 | -0.02 | -0.01 | -0.02 | -0.01 |

TIME [msec]    STRAIN VALUE ns
ULTRASONIC DIAGNOSTIC DEVICE AND IMAGE PROCESSING DEVICE

CROSS-REFERENCE TO RELATED APPLICATIONS

This application is based upon and claims the benefit of priority from prior Japanese Patent Application No. 2005-302189, filed Oct. 17, 2005, the entire contents of which are incorporated herein by reference.

BACKGROUND OF THE INVENTION

1. Field of the Invention

The present invention relates to an ultrasonic diagnostic device and an image processing device that are capable of imaging the strain of tissue.

2. Description of the Related Art

An ultrasonic diagnostic device includes an ultrasonic transmission and reception control unit that controls the ultrasonic transmission and reception, an ultrasonic transmitting and receiving unit that transmits and receives ultrasonic waves to and from an object to be examined, a tomographic scanning unit that repeatedly obtains tomographic image data in the object including moving tissue in a predetermined period, by using a reflective echo signal from the ultrasonic transmitting and receiving unit, and an image display unit that displays time series tomographic image data obtained by the tomographic scanning unit. The structure of a biomedical tissue inside the object is displayed as a B-mode image.

On the contrary, recently, a TSI (tissue strain imaging) method that images how much strain is generated in a predetermined tissue in a predetermined time is known. According to the TSI method, it is possible to quantitatively show the change in the strain using a graph by setting a ROI (region of interest) in a position of interest.

However, since the strain of the tissue is affected by various factors such as the tissue shape or the compression speed, it is difficult to quantitatively evaluate the strain. As one example of the quantitative evaluation methods, a result that introduced the examination of the strain ratio was reported (for example, refer to Jpn. J. Med. Ultrasonics, Vol. 32, Supplement (2006) P292). According to the report, when the linearity of the strain is formed by the compression, there is a possibility that the ratio of the interest portion serves as an indicator of the diagnosis. However, the display or treatment of the data concerning the diagnosis or setting the ROI is not disclosed.

Further, it is possible to draw a graph that quantitatively represents the change of the strain by setting the ROI into the position of interest and to output the strain value in a specified range with respect to the ROI set by a user (refer to FIG. 4) as a text. In FIG. 4, the strain values of six ROIs are measured at regular time intervals. Therefore, it is possible to manually calculate the strain ratio of two different ROIs on the basis of strain values of ROIs output at regular time intervals.

However, in order to obtain the strain ratio of the two different ROIs, the user calculates the strain ratio on the basis of text information by himself. Therefore, there are problems in that it takes a lot of work or time to calculate the strain ratio and errors are unavoidable when setting various ROIs.

BRIEF SUMMARY OF THE INVENTION

Accordingly, an object of the present invention is to provide an ultrasonic diagnostic apparatus and an image processing apparatus that are capable of easily confirming the strain ratio of two different ROIs.

This invention displays the strain values of two ROIs by appointing the two ROIs, and displays the strain ratio as a numerical value. To be more specific, this invention is as follows.

An aspect of the invention includes a means to which at least two ROIs are input, a calculating means that calculates strain values of tissue with respect to the at least two ROIs by applying a pressure onto an object, and a display means that displays the strain values of the at least two ROIs so as to be compared with each other.

Additional objects and advantageous of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a diagram showing an example of strain values of ROIs in a specified range that are output as a text.

DETAILED DESCRIPTION OF THE INVENTION

Preferred embodiments of this invention will be described with reference to accompanying drawings.

Figure 1:
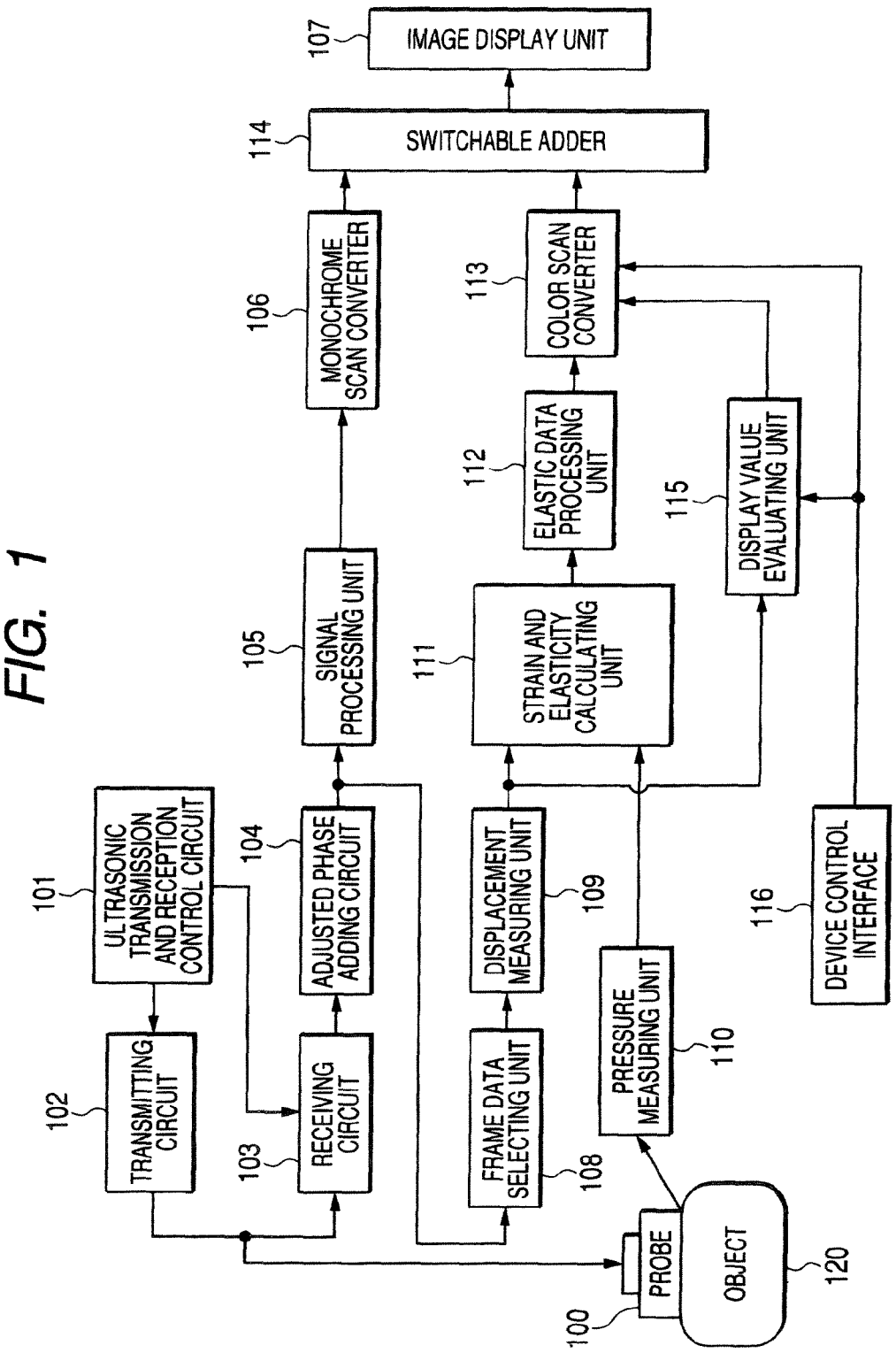
FIG. 1 is a block diagram showing a schematic configuration of an ultrasonic diagnostic apparatus according to an embodiment of this invention.

FIG. 1 is a block diagram showing a schematic configuration of an ultrasonic diagnostic apparatus according to an embodiment of this invention. The ultrasonic diagnostic apparatus according to the embodiment obtains a tomographic image of an ROI (region of interest) of an object by using an ultrasonic wave, and displays an elastic image that represents the hardness or tenderness of a biomedical tissue. As shown in FIG. 1, the ultrasonic diagnostic apparatus includes an ultrasonic probe 100, an ultrasonic transmission and reception control unit 101, a transmitting circuit 102, a receiving circuit 103, an adjusted phase adding circuit 104, a signal processing unit 105, a monochrome scan converter 106, an image display unit 107, a frame data selecting unit 108, a displacement measuring unit 109, a pressure measuring unit 110, a strain and elasticity calculating unit 111, an elastic data processing unit 112, a color scan converter 113, a switchable adder 114, a display value evaluating unit 115, and a device control interface 116. With this configuration, data of both the elasticity and the strain value can be obtained. However, the elasticity is a ratio of the increment of stress and the increment of strain, and the strain is a variation of a length of a material in a direction with respect to a length that is not distorted in a direction (both directions do not need to be equal to each other). This invention mainly displays a ratio of strains (hereinafter, referred to as strain ratio) in at least two ROIs. Therefore, it does not need to calculate the elasticity, and thus the pressure measuring unit 110 is not needed. However, since it may need to detect an error portion by calculating the elasticity, the pressure measuring unit 110 is shown in FIG. 1, and the description of the pressure measuring unit 110 will be added so that the case when both the strain and the elasticity are calculated will be described.

The ultrasonic probe 100 is formed such that a plurality of vibrators are arranged in an array shape, and performs mechanic or electronic beam scanning to transmit or receive the ultrasonic wave to or from the object 120. The ultrasonic probe 100 is mounted with a vibrator (not shown) that is an ultrasonic wave source and receives a reflective echo. In here, when a pressuring plate is provided so as to face an ultrasonic wave transmitting and receiving face of the ultrasonic probe 100 and a surface of the pressuring plate, the pressuring face formed between the ultrasonic wave transmitting and receiving face and the pressuring plate contacts a main surface of the object and then moves the pressuring face to pressure the object. Therefore, while transmitting or receiving the ultrasonic wave by the ultrasonic probe 100, the stress of the ROI of the object 120 can be effectively analyzed in a body cavity. Further, the pressuring plate does not always need to be used, and it is possible to obtain the strain value by repetitively and manually pressing or releasing the object using the ultrasonic probe 100 by the user.

The ultrasonic transmitting and receiving control unit 101 controls the timing of transmitting and receiving the ultrasonic wave. The transmitting circuit 102 generates a transmitting pulse for driving the ultrasonic probe 100 to generate the ultrasonic wave, and sets a focusing point of the ultrasonic wave transmitted from the transmitted adjusted phase adding circuit mounted therein to have a predetermined depth. The receiving circuit 103 amplifies the reflective echo signal received by the ultrasonic probe 100 to have a predetermined gain. The number of amplified reflected signals corresponding to the number of vibrators is input to the adjusted phase adding circuit 104 as separate receiving signals. The reception signal amplified in the receiving circuit 103 is inputted to the phase adding circuit 104, and the phases are controlled and the ultrasonic beams are formed so as to correspond to one or a plurality of focusing points. The signal processing unit 105 inputs the receiving signal from the adjusted phase adding circuit 104 to perform various signal processings such as gain correction, log compression, detection, edge enhancement, filtering, etc.

The ultrasonic probe 100, the ultrasonic transmitting and receiving control unit 101, the transmitting circuit 102, the receiving circuit 103, the adjusted phase adding circuit 104, and the signal processing unit 105 form an ultrasonic transmitting and receiving means, and one tomographic image of the object 120 is obtained by scanning the ultrasonic beam using the ultrasonic probe 100 in a specific direction of the object 120.

The monochrome scan converter 106 obtains frame data in the object 120 including the moving tissue using the reflective echo signal output from the signal processing unit 105 in an ultrasonic period, and reads the frame data as a television signal so as to display it.

The image display unit 107 displays a time series tomographic image data, that is, a B mode tomographic image obtained by the monochrome scan converter 106. Specifically, the image display unit 107 includes a D/A converter that converts the image data output from the monochrome scan converter 106 via the switchable adder 114 into an analog signal and a color television monitor that inputs the analog video signal from the D/A converter to display the signal as an image.

The frame data selecting unit 108 and the displacement measuring unit 109 are branched from the output side of the adjusted phase adding circuit 104 and the pressure measuring unit 110 is provided parallel to the frame data selecting unit 108 and the displacement measuring unit 109. The strain and elasticity calculating unit 111 is provided behind the pressure measuring unit 110 and the displacement measuring unit 109. The display value evaluating unit 115 is branched from the output side of the displacement measuring unit 109, and the elastic data processing unit 112 and the color scan converter 113 are provided behind the strain and elasticity calculating unit 111. Further, the switchable adder 114 is provided at the output side of the monochrome scan converter 106 and the color scan converter 113. The display value evaluating unit 115 and the color scan converter 113 are easily controlled through the device control interface 116 by a user.

The frame data selecting unit 108 sequentially stores frame data sequentially output from the adjusted phase adding circuit 104 at a frame rate of the ultrasonic diagnostic apparatus, in a frame memory provided in the frame data selecting unit 108 (currently stored frame data is referred to as frame data N), and selects one of the frame data among past frame data N-1, N-2, N-3, . . . N-M (referred to as frame data X) in accordance with the control command of the ultrasonic diagnostic apparatus to output a set of frame data N and frame data X to the displacement measuring unit 109. Even though the signal output from the adjusted phase adding circuit 104 is referred to as frame data, the signal may be a complex demodulated I, Q signal.

The displacement measuring unit 109 performs a one dimensional or two dimensional correlation processing on the basis of the set of frame data selected by the frame data selecting unit 108, measures the displacement of the measuring point on the tomographic image or moving vector (the direction and the size of the displacement), and generates displacement frame data.

The pressure measuring unit 110 measures or estimates the pressure in the body cavity of the object 120. Specifically, the pressure measuring unit 110 measures how strong pressure is applied between the probe head of the ultrasonic diagnostic apparatus 100 and the object 120, for example, a pressure sensor that detects pressure applied into the rod shape member is mounted at the side of the probe head, the pressure between the probe head and the object 120 is measured at an arbitrary time phase, and the measured pressure is transmitted to the strain and elasticity calculating unit 111. When it does not need to calculate the elasticity, the pressure measuring unit 110 is not needed, as described above. Therefore, even though the pressure measuring unit 110 may be omitted, the pressure measuring unit 110 is shown in FIG. 1 in consideration with the case when calculating the elasticity.

The strain and elasticity calculating unit 111 calculates the strain of the measuring points on the tomographic image of the displacement frame data (the amount of movement) output from the displacement measuring unit 109 and the pressure measuring unit 110 to generate numerical data (hereinafter, referred to as elastic frame data) and outputs to the elastic data processing unit 112. In order to calculate the strain, the strain is preferably calculated using the displacement obtained by integrating the speed of the tissue, on the basis of a Doppler signal without using the displacement frame data. Further, it is preferable that the displacement measuring unit 109 inputs pressure data output from the pressure measuring unit 109 to calculate the elasticity of the measuring points on the tomographic image and output the numerical data to the elastic data processing unit 112.

The elastic data processing unit 112 performs various image processings such as a smoothing process of the elastic frame data from the strain and elasticity calculating unit 111 in the coordinate plane, a contrast optimizing process, a smoothing process of an inter-frame in the time axial direction, etc., and outputs the processed elastic frame data to the color scan converter 113.

The color scan converter 113 includes a color information converting means that assigns color information such as red, green, blue, etc. to the elastic frame data output from the elastic data processing unit 112, and elastic image data from a command by the ultrasonic diagnostic apparatus, or the elastic frame data output from the elastic data processing unit 112. In detail, in a region having a large measured strain of the elastic frame data output from the elastic data processing unit 112, the corresponding region in the elastic image data is converted into a red code, and in a region having a small measured strain, the corresponding region in the elastic image data is converted into a blue code. Further, the color scan converter 113 may be a monochrome scan converter, and in the region having large strain, the brightness of the corresponding region in the elastic data may be large, and in the region having small strain, the brightness of the corresponding region in the elastic data may be small.

The switchable adder 114 inputs monochrome tomographic image data from the monochrome scan converter 106 and the color elastic image data from the color scan converter 113 and adds or switches both image data. Therefore, it is possible to switch between the output of only one of the monochrome tomographic image data and the color elastic image data and the output of the composition of both image data. For example, it is preferable to simultaneously display the monochrome tomographic image and a color or monochrome elastic image by the monochrome scan converter in two screen displays. It is further preferable to display by translucently overlapping the monochrome tomographic image and the color elastic image. Therefore, the image data output from the switchable adder 114 outputs to the image display unit 107.

Figure 2:
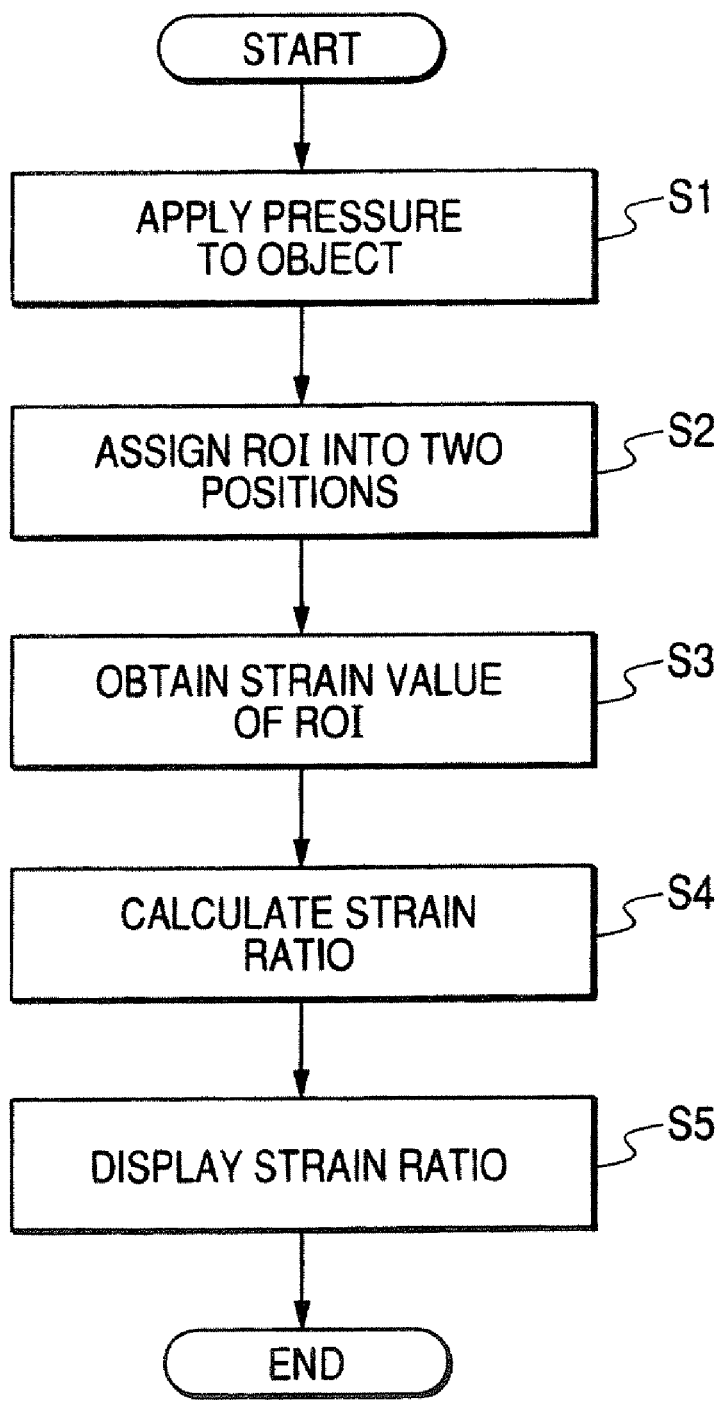
FIG. 2 is a flowchart showing an operation of the ultrasonic diagnostic apparatus according to the embodiment of this invention.

A method according to the embodiment that is applied to the ultrasonic diagnostic apparatus with the above configuration will be described with reference to FIGS. 2 and 3. FIG. 2 is a flowchart showing an operation of the ultrasonic diagnostic apparatus according to the embodiment of this invention, and FIG. 3 is a view showing an example that represents a graph of a strain image and a strain value (including a strain ratio) as an image.

Figure 3:
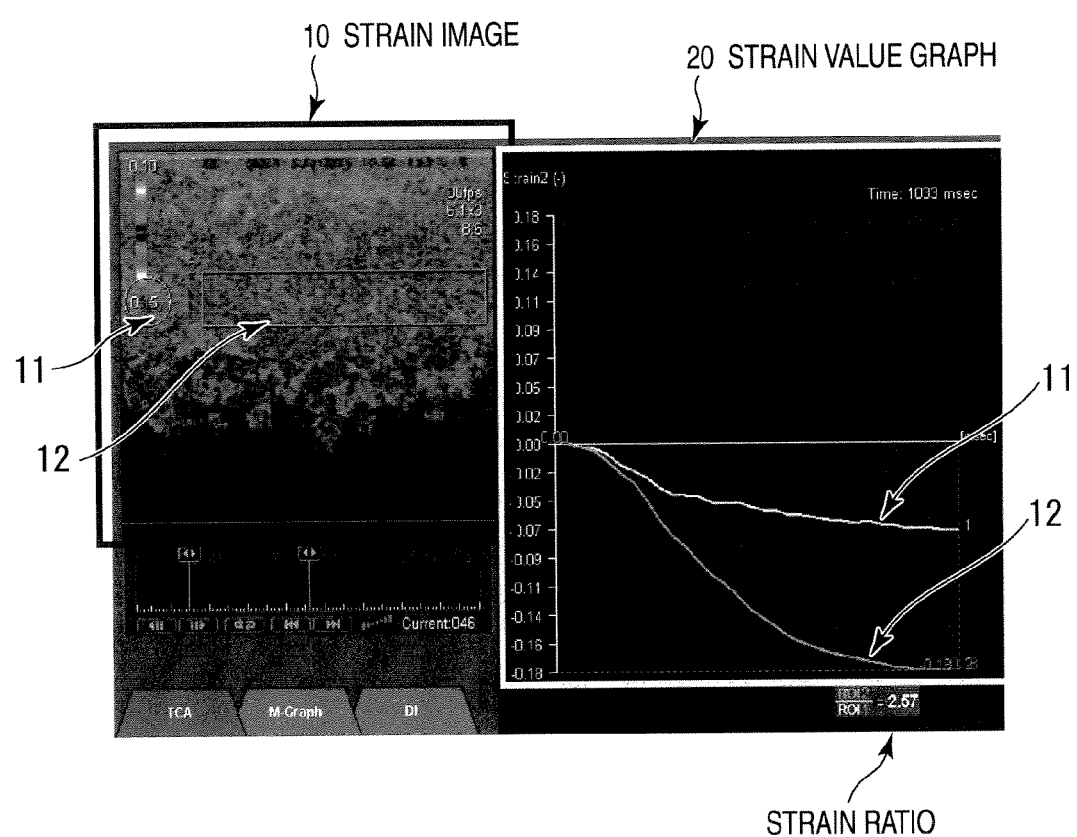
FIG. 3 is a view showing an example that represents a graph of a strain image and a strain value (including a strain ratio) as an image.

In the case when obtaining a strain image in the ultrasonic diagnostic apparatus while applying the pressure onto the object 120, when the strain image 10 as shown on the left side of FIG. 3 is observed, what is displayed is a portion denoted by reference numeral 11 has a strain value different from the neighboring portions. At first, a strain image is obtained while gradually applying a constant pressure onto the object 120 to which pressure has not been applied (step S1). The strain image, for example, is displayed as a color image corresponding to the strain value (for example, the saturation or brightness is changed depending on the magnitude of strain value). Two ROIs of a first ROI 11 and a second ROI 12 are assigned through the device control interface 116 by the user on the basis of the strain image (step S2). The assigned two ROIs are ROIs whose strain ratio is wanted to be known. Then, the strain values of the assigned ROIs are obtained at predetermined time intervals (step S3). In this case, it is preferable to apply the pressure so as to be proportional to the time. Therefore, the strain value graph 20 is obtained. Further, in the strain value graph 20 of FIG. 3, the vertical axis is a strain value obtained by the image and the horizontal axis is a time passing after measuring (or after applying the pressure).

The strain ratio of the two ROIs is calculated using the obtained strain value (step S4), and the result (in FIG. 3, the second ROI/the first ROI=2.57) is displayed on the image display unit 107 (step S5). Further, the timing of calculating the strain ratio can be arbitrarily set, as long as the strain ratio can be exactly calculated. For example, in FIG. 3, the strain value is calculated at the time of applying the pressure for 1033 mm seconds. However, in this case, since the strain values of the first ROI 11 and the second ROI 12 are different from each other by around 500 mm sec, it is preferable that the user stops applying the pressure at that timing and calculates the strain value. Further, the display of the strain value graph 20 and the strain ratio may be appropriately updated with the passage of the time (that is, in accordance with the pressure). Further, the update timing is appropriately set by the user.

In the graph of the strain of the first ROI 11 and the second ROI 12, if the time has sufficiently passed, even though the pressure is applied, the strain value does not increase, that is, the strain value becomes a saturated (normal) state. Since the strain ratio in this state becomes a strain ratio of the first ROI 11 and the second ROI 12, it is possible to obtain a stable strain ratio. Therefore, by reflecting the strain ratio onto the image 10, it is possible to improve the accuracy of the diagnosis.

According to this invention, it is possible to confirm the strain ratio of two ROIs as a numerical value. Especially, in the ultrasonic diagnostic apparatus, when the strain ratio is used in a tissue elastic imaging method, it is possible to be able to know the difference in hardnesses between a tumor portion and a normal portion, and easily diagnose as such. Further, by reflecting the strain ratio onto the strain image 10, since it is possible to visibly confirm the amount of strain between the ROIs, it is possible to improve the accuracy of the diagnosis.

This invention is not limited to the above embodiment, and it is possible to perform various modifications in a range without departing from the gist of this invention.

For example, in the above embodiment, even though the pressure increase in accordance with the passage of the time, the total strains from the time when starting to apply the pressure to the time when releasing the pressure are measured, and the strain ratio may be calculated to be displayed. In this case, the graph is expected that the coefficient is positive in the strain value graph 20 of FIG. 3.

Further, in FIG. 3, the shape of the first ROI 11 is a circle, and the shape of the second ROI 12 is a rectangular. However, the shape is not limited thereto, and both ROIs may be a circle, or rectangular. Further, the shape of the ROIs may be any shape other than a circle or rectangular (for example, triangular, oval, etc.) or may be an arbitrary shape drawn by a user with, for example, a pointing device, as long as the region of the ROI is exactly shown.

In the above embodiment, even though the indication of ROI is performed with respect to the two ROIs, the number of ROIs may be three or more, and the ROIs may be appropriately indicated corresponding to the diagnosis purpose.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ultrasonic diagnostic apparatus comprising:
   an input unit to which at least two ROIs (Region of Interest(s)) are input;
   a calculating unit that calculates strain values of tissue with respect to the at least two ROIs by applying a pressure onto an object; and
   a display unit configured to display on a single screen an image in colors depending on the strain values of the at least two ROIs with a corresponding strain value/time graph for each of the at least two ROIs.

2. The ultrasonic diagnostic apparatus according to claim 1,
   wherein the calculating unit calculates a ratio of the strain values of the at least two ROIs (Region of Interest(s)), and the display unit displays the ratio of the strain values of the at least two ROIs calculated by the calculating unit.

3. The ultrasonic diagnostic apparatus according to claim 2,
   wherein the display unit displays the ratio of the strain values as a numerical value.

4. The ultrasonic diagnostic apparatus according to claim 2,
   wherein the display unit displays the ratio of the strain values when all of the strain values of the ROIs (Region of Interest(s)) are constant.

5. The ultrasonic diagnostic apparatus according to claim 2,
   wherein the display unit changes the ROIs (Region of Interest(s)) depending on the value of the strain ratio to display.

6. The ultrasonic diagnostic apparatus according to claim 1,
   wherein a shape of each ROI (Region of Interest(s)) includes a circle, a rectangular, an oval, or a shape drawn by a user.

7. The ultrasonic diagnostic apparatus according to claim 1,
   wherein the ROIs are three or more.

8. The ultrasonic diagnostic apparatus according to claim 1,
   wherein the display unit updates the display with passage of time.

9. An image processing apparatus utilized in an ultrasonic diagnostic apparatus that images a strain of a tissue, comprising:
   an input unit to which at least two ROIs (Region of Interest(s)) are input;
   a calculating unit that calculates strain values of tissue with respect to the at least two ROIs by applying a pressure onto an object; and
   a display unit configured to display on a single screen an image in colors depending on the strain values of the at least two ROIs with a corresponding strain value/time graph for each of the at least two ROIs.

* * * * *